(12) United States Patent
Myers

(10) Patent No.: US 11,458,074 B2
(45) Date of Patent: Oct. 4, 2022

(54) VESSEL FOR BREAST MILK COLLECTION, PRESERVATION, TRANSPORTATION, AND DELIVERY

(71) Applicant: Ceres Chill, Inc., Bainbridge Island, WA (US)

(72) Inventor: Elizabeth Joy Myers, Bainbridge Island, WA (US)

(73) Assignee: Ceres Chill, Inc., Bainbridge Island, WA (US)

(*) Notice: Subject to any disclaimer, the term of this patent is extended or adjusted under 35 U.S.C. 154(b) by 313 days.

(21) Appl. No.: 16/684,452

(22) Filed: Nov. 14, 2019

(65) Prior Publication Data

US 2020/0155418 A1 May 21, 2020

Related U.S. Application Data

(60) Provisional application No. 62/768,867, filed on Nov. 17, 2018.

(51) Int. Cl.
*A61J 9/08* (2006.01)
*A61M 1/06* (2006.01)
(Continued)

(52) U.S. Cl.
CPC .................. *A61J 9/085* (2013.01); *A61J 9/06* (2013.01); *A61J 11/04* (2013.01); *A61M 1/062* (2014.02);
(Continued)

(58) Field of Classification Search
CPC .......... A61J 2200/50; A61J 9/085; A61J 9/06; A61J 9/00; A61J 9/016; A61J 11/04;
(Continued)

(56) References Cited

U.S. PATENT DOCUMENTS 4,747,501 A * 5/1988 Greaves ............... B65D 51/223
220/276
4,815,287 A 3/1989 O'Daniel
(Continued)

FOREIGN PATENT DOCUMENTS

CN 201591845 U 9/2010
CN 204351521 * 5/2015
(Continued)

OTHER PUBLICATIONS

International Search Report and Written Opinion of the International Searching Authority dated Apr. 16, 2020, issued in corresponding International Application No. PCT/US2019/061539, filed Nov. 14, 2019, 10 pages.

(Continued)

*Primary Examiner* — James N Smalley
*Assistant Examiner* — Jennifer Castriotta
(74) *Attorney, Agent, or Firm* — Perkins Coie LLP

(57) ABSTRACT

A vessel includes an inner container, an outer container, a connector, a cap, and a lid. The outer container includes a first coupler and an outer chamber. The inner container includes a second coupler and an inner chamber to hold a liquid. The inner container is receivable at least partially within the outer chamber. The connector includes a third coupler that is complementary to the first coupler, and a fourth coupler that is complementary to the second coupler. When both the first coupler is engaged with the third coupler and the second coupler is engaged with the fourth coupler, the outer chamber is entirely enclosed within a liquid-proof barrier.

14 Claims, 10 Drawing Sheets

(51) Int. Cl.
*A61J 9/06* (2006.01)
*A61J 11/04* (2006.01)
*B65D 51/28* (2006.01)

(52) U.S. Cl.
CPC ........... *B65D 51/28* (2013.01); *A61J 2200/44* (2013.01); *A61J 2200/50* (2013.01); *B65D 2251/09* (2013.01)

(58) Field of Classification Search
CPC ............ B65D 81/3227; B65D 81/3216; B65D 51/28; B65D 2251/09
USPC .......................................... 220/737, 739, 740
See application file for complete search history.

(56) References Cited

U.S. PATENT DOCUMENTS

| | | | |
|---|---|---|---|
| 4,981,022 A | | 1/1991 | Snyder |
| 5,009,083 A | * | 4/1991 | Spinos ................. A47G 21/187 62/457.3 |
| 5,156,284 A | | 10/1992 | Del et al. |
| 5,467,877 A | | 11/1995 | Smith |
| 5,875,646 A | | 3/1999 | Rich |
| 5,943,875 A | | 8/1999 | Hymes |
| 6,123,065 A | | 9/2000 | Teglbjarg |
| 6,415,624 B1 | | 7/2002 | Connors et al. |
| 7,093,459 B2 | | 8/2006 | Citrynell et al. |
| 9,248,077 B1 | | 2/2016 | Kelly et al. |
| 10,196,186 B2 | * | 2/2019 | Cox .................... B65D 47/2031 |
| 10,271,670 B2 | * | 4/2019 | Heiman ............. A47G 19/2272 |
| 2002/0108394 A1 | | 8/2002 | Holley |
| 2006/0191283 A1 | | 8/2006 | Overgaard |
| 2007/0175237 A1 | | 8/2007 | Roth et al. |
| 2008/0000259 A1 | | 1/2008 | Shewchuk |
| 2008/0041859 A1 | | 2/2008 | Teglbjarg |
| 2009/0250478 A1 | | 10/2009 | Roth et al. |
| 2010/0025350 A1 | | 2/2010 | Kenney |
| 2012/0298675 A1 | | 11/2012 | Archie et al. |
| 2015/0122765 A1 | | 5/2015 | Cannon et al. |
| 2017/0297787 A1 | * | 10/2017 | Defert .................. B65D 51/225 |
| 2017/0355508 A1 | * | 12/2017 | Currington .......... B65D 51/222 |

FOREIGN PATENT DOCUMENTS

| | | |
|---|---|---|
| CN | 204351521 U | 5/2015 |
| EP | 0265048 A2 | 4/1988 |
| KR | 200476483 Y1 | 3/2015 |

OTHER PUBLICATIONS

Examination Report dated May 13, 2022 in United Kingdom Patent Application No. GB2106808.5, 3 pages.

Office Action dated Apr. 22, 2022 in Chinese Patent Application No. 201980075274.8, 17 pages, with English translation.

* cited by examiner

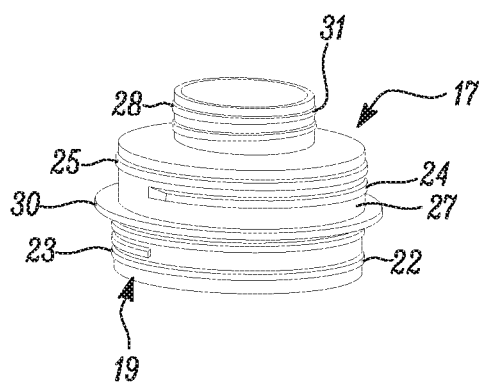
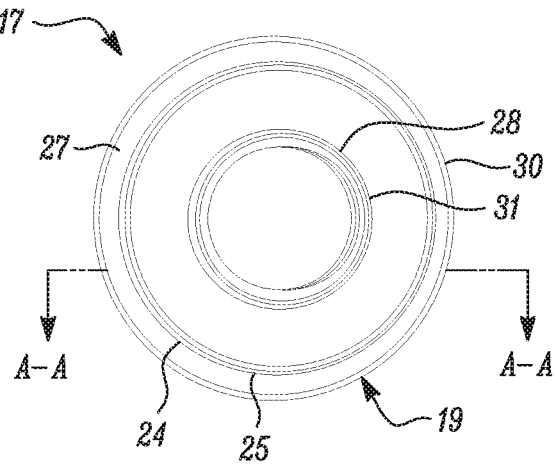
FIG. 4    FIG. 5
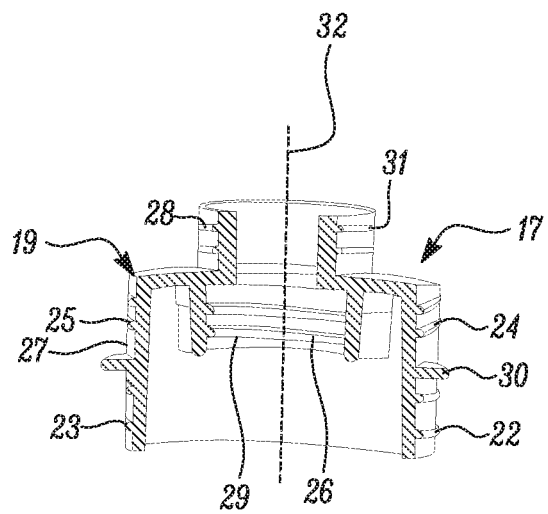
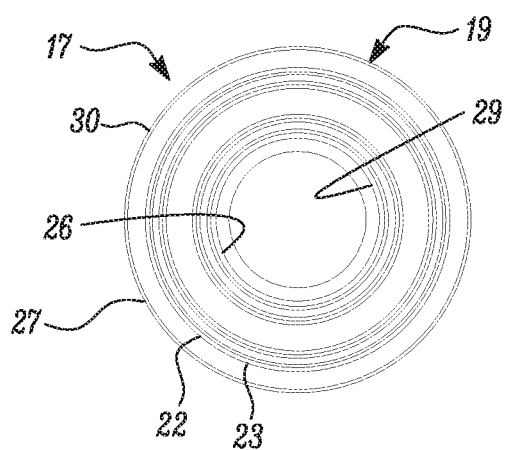
FIG. 6    FIG. 7

VESSEL FOR BREAST MILK COLLECTION, PRESERVATION, TRANSPORTATION, AND DELIVERY

BACKGROUND

Technical Field

The present disclosure relates generally to food and beverage storage containers, and specifically to a container for safe, temperature modifying and extended storage of breast milk to enable uncontaminated transport and use of unspoiled breast milk.

Description of the Related Art

Known bottles, food storage containers, carafes and thermoses are designed to maintain contents at a cold or hot temperature. There are limited examples of food safe containers that provide for warm contents to be safely cooled without dilution and then maintained at a safe, chilled temperature. Known products incorporate a design that risks contamination of breast milk by inserting a cooling rod into the milk or surrounding the milk container with unsafe chemicals. Other known containers are directed at the consumption of alcohol, coffee or soft drinks.

Medical professionals regularly instruct caregivers that expressed milk should be stored in a clean, capped glass or hard plastic, BPA-free container or special plastic bags designed for milk collection and storage. However, online medical resources also warn that breast milk storage bags may tear, leak, open and become contaminated more easily than hard-sided containers. Known hard containers cannot be used for breast milk storage without refrigeration and bags are problematic for the reasons listed herein.

As a result of the deficiencies of known products, women do not have a safe container into which they can directly pump and store their breast milk for more than four hours. Women are therefore forced to undertake pumping into multiple small containers that need to be refrigerated or stored in portable coolers. Alternatively, women must dispose of their milk if they are without refrigeration while traveling, working or otherwise unable to directly breastfeed a child.

Accordingly, it is desirable to provide a new apparatus and associated method to collect, cool, and preserve nutrient rich breast milk and reduce or prevent said breast milk from being wasted, and to provide women and caregivers the ability to overcome numerous obstacles to pumping, transporting, storing and feeding breast milk.

BRIEF SUMMARY

According to one aspect of the disclosure, a vessel includes an outer container, an inner container, and a connector. The outer container has a first coupler and an outer chamber. The inner container has a second coupler and an inner chamber to hold a liquid, and the inner container is receivable at least partially within the outer chamber such that a gap is formed between the inner container and the outer container. The connector has a third coupler that is complementary to the first coupler, and a fourth coupler that is complementary to the second coupler. When both the first coupler is engaged with the third coupler and the second coupler is engaged with the fourth coupler, the outer chamber is entirely enclosed within a liquid-proof barrier.

According to another aspect of the invention a connector includes a first coupler, a second coupler, and a third coupler. The first coupler is complementary to a complementary coupler, and the second coupler is complementary to the same complementary coupler. The third coupler is different than the first coupler and the second coupler such that the third coupler is not complementary to the complementary coupler. The first coupler is discontinuous with the second coupler such that the complementary coupler cannot transition from engagement with the first coupler to engagement with the second coupler without first disengaging from the connector.

According to another aspect of the invention a method of pumping and storing breast milk includes contacting a breast shield with a breast, and while contacting the breast with the breast shield, applying suction to the breast, thereby withdrawing milk from the breast. The method further includes transferring the withdrawn milk from the breast to an inner chamber of an inner container, the inner container coupled to the breast shield by a first connector. The method further includes decoupling the inner container from the breast shield by disengaging the first connector from the inner container, depositing a cooling medium into an outer chamber of an outer container, coupling the inner container to a second connector such that the inner chamber is enclosed, inserting the inner container into the outer chamber, and after coupling the inner container to the second connector, coupling the outer container to the second connector such that a gap is formed between the inner container and the outer container, at least a portion of the gap occupied by the cooling medium.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not necessarily drawn to scale, and some of these elements may be arbitrarily enlarged and positioned to improve drawing legibility. Further, the particular shapes of the elements as drawn, are not necessarily intended to convey any information regarding the actual shape of the particular elements, and may have been solely selected for ease of recognition in the drawings.

FIG. 4 is an isometric view of a connector of the container illustrated in FIG. 1, according to one embodiment.

FIG. 5 is a top, plan view of the connector illustrated in FIG. 4.

FIG. 6 is a cross-sectional view, of the connector illustrated in FIG. 4, along line A-A.

FIG. 7 is a bottom plan view of the connector illustrated in FIG. 4.

DETAILED DESCRIPTION

Figures 1, 2:
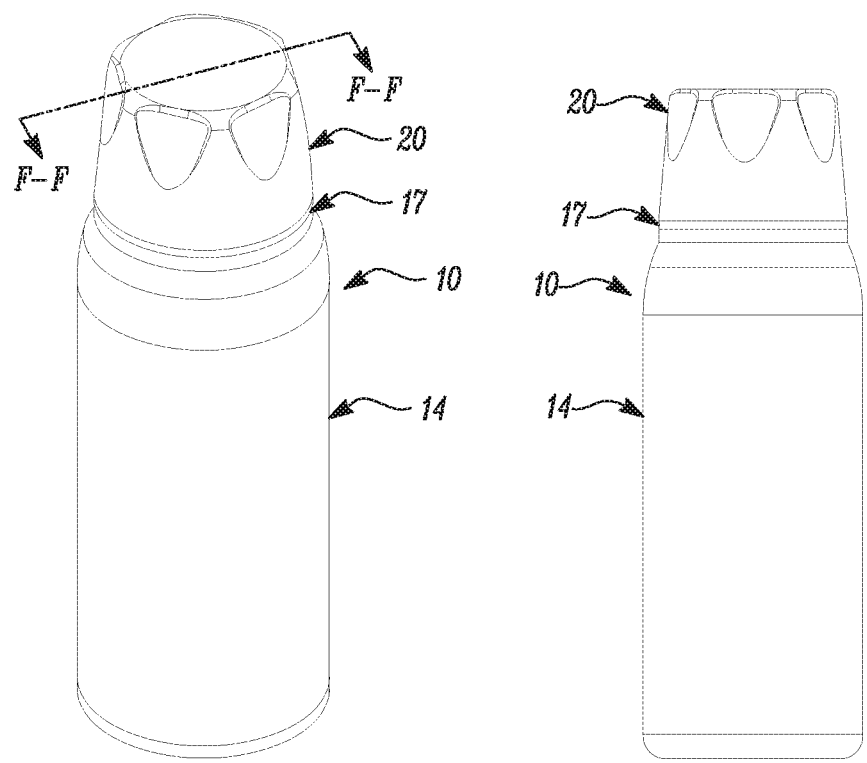
FIG. 1 is an isometric view of a container, according to one embodiment.
FIG. 2 is a side, elevation view of the container illustrated in FIG. 1.

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with liquid containers have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment," "an embodiment," or "an aspect of the disclosure" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its broadest sense, that is as meaning "and/or" unless the content clearly dictates otherwise.

Reference herein to two elements "facing" or "facing toward" each other indicates that a straight line can be drawn from one of the elements to the other of the elements without contacting an intervening solid structure. Reference herein to two elements being "coupled" indicates that relative movement of one of the elements relative to the other of the elements is restricted, for example blocked, in at least one degree of freedom. Reference herein to two elements being "directly coupled" indicates that the two elements physically touch with no intervening structure between.

Reference herein to a direction includes both vectors that make up said direction. For example a longitudinal direction includes both a "distal" vector and a "proximal" vector, which is opposite the "distal" vector. Reference to an element extending along a direction means the element extends along one or both of the vectors that make up the direction.

The term "aligned" as used herein in reference to two elements along a direction means a straight line that passes through one of the elements and that is parallel to the direction will also pass through the other of the two elements. The term "between" as used herein in reference to a first element being between a second element and a third element with respect to a direction means that the first element is closer to the second element as measured along the direction than the third element is to the second element as measured along the direction. The term "between" includes, but does not require that the first, second, and third elements be aligned along the direction.

Recitation of ranges of values herein are merely intended to serve as a shorthand method of referring individually to each separate value falling within the range including the stated ends of the range, unless otherwise indicated herein, and each separate value is incorporated into the specification as if it were individually recited herein.

Aspects of the disclosure will now be described in detail with reference to the drawings, wherein like reference numbers refer to like elements throughout, unless specified otherwise. Certain terminology is used in the following description for convenience only and is not limiting. The term "plurality", as used herein, means more than one. The terms "a portion" and "at least a portion" of a structure include the entirety of the structure.

The headings and Abstract of the Disclosure provided herein are for convenience only and do not interpret the scope or meaning of the embodiments.

Referring to FIGS. 1 to 22, a vessel 10 for liquid collection, preservation and transportation is disclosed herein. According to one aspect of the disclosure, the vessel 10 is used to assist in the process of collecting, preserving, and transporting pumped breast milk, and the feeding of said pumped breast milk to a child. The advantages of the vessel 10 are numerous including, but not limited to: health and wellness; lifestyle; financial; and environmental. Whereas users previously had to undertake multiple pumpings into multiple containers (small bottles, bags, sealable containers), users of the vessel 10 can pump into one larger container. This allows for a healthy mix of "foremilk," which is lower fat/caloric milk, with higher fat "hindmilk." This ability to provide a more natural feeding mix significantly benefits the health of the child.

Multiple pumpings and transferring pumped breast milk between multiple containers also increases the risk of contamination and spills/loss of volume. Many women have trouble producing enough milk when not directly breastfeeding so any loss of volume is a problem and discouraging. The most common containers into which users can pump are plastic. Many consumers are concerned that plastics contaminate contents. Soft plastics are generally not as durable and safe as other materials such as glass, stainless steel, and hard plastics.

Known breast milk storage containers include coolers that are inconvenient, more difficult to transport, indiscreet, and require several components (cooler, bags, bottles, chilled package, etc.). The vessel 10 allows for easy, safe transport.

The vessel 10 may include an attractive aesthetic appearance, and may look similar to other water bottles or hot beverage containers. Users of the vessel 10 may be able to keep the vessel 10 on their person, in their offices or otherwise in plain sight without others knowing that the user is lactating, pumping and transporting breast milk. The vessel 10 may be sized and shaped so as to be easily transported by carrying it or putting it in bags, briefcases or luggage.

Caregivers may encounter difficulty and inconvenience when trying to safely transport breast milk while away from refrigeration. This difficulty impedes the non-breastfeeding caregiver's ability to go out of the home with breastfeeding children. The vessel 10 allows for breast milk to be easily carried separately or packed in a diaper bag/backpack, safely stored for hours and then used to feed a child as needed. The separate component to warm and deliver a portion of the milk for feeding allows for the other unused portion of the breast milk to be preserved without contamination.

Known containers require the use of disposable bags and semi-permanent bottles. Almost all of the bags cannot safely be reused and must be disposed of after every use. As a result, breast pumping users must continuously purchase bags which are then thrown away after each use. The vessel 10 allows for transport of breast milk in one large, reusable container that can be used for regular (non-breast milk) beverage cooling or warming transport and consumption long after the breast pumping user has finished breastfeeding children. Unlike the plastic bags and bottles, the vessel 10, according to one embodiment, may be a versatile, attractive, durable, re-usable container that is safe for long-term food/beverage transportation and consumption use.

The vessel 10 provides a solution that significantly overcomes the shortcomings of prior, existing devices and methods for breast milk storage, transport and feeding. The vessel 10 disclosed herein is a container configured to allow a user to pump breast milk directly into a container capable of cooling warm breast milk down to a safe storage temperature and maintaining it at a safe temperature for several hours without dilution. According to one embodiment, the vessel 10 may be an insulated, double chambered bottle with at least an eight ounce capacity. The vessel 10 may include a removable inner container 12 with a threaded neck that is compatible with breast pump attachments to allow for milk to be expressed directly into the inner container.

When the vessel 10 is not being used for collecting expressed milk, the inner container 12 threaded neck may be sealed with a cap 18 that can be coupled to the inner container 12 to enclose an inner chamber 46 of the inner container 12, or removed from the inner container 12 to open the inner chamber 46 to a surrounding environment. The vessel 10 may include a lid 20, which serves to prevent contamination of the breast milk within the inner chamber and provides an "on-the-go" feeding bottle.

One advantage of the vessel 10 is that the size of the inner chamber 12 allows users to pump breast milk in excess of the two to eight ounce limit currently found in known breast milk containers. The breast milk may be pumped directly into one container, which is a safe storage container that lowers and maintains the milk at a safe temperature without dilution. The lid 20 covering the cap 18 protects the pour top and threaded neck from contaminants while also serving as a versatile, warmable feeding bottle.

The vessel 10 may include an outer container 14 which includes a second, or outer, chamber 96 that can be filled with a coolant such as frozen water. Thus, the design of the vessel 10 may provide a means to cool expressed breast milk and maintain it at a safely chilled temperature until it can be transported to feed a child or to be maintained for longer periods in refrigeration.

The inner chamber 46 and the outer chamber 96 of the vessel 10 may be configured such that the contents within the inner chamber 46, for example expressed breast milk, are cooled by a freezable/cold outer chamber 96. The outer chamber 96 may be externally insulated to prevent condensation and heat exchange with environmental temperatures surrounding the vessel 10. The contents within the inner chamber are able to become cool and remain at a chilled storage temperature for more than six hours without dilution.

The connector 17, according to one embodiment, may include a threaded neck to accommodate breast pump components. When breast pump equipment is not in use, the cap 18 may be used to close the pour top opening of the inner container 12. Cooled milk may be poured from the inner chamber 46 of the inner container 12 into the lid 20 as will be described in greater detail below. The lid 20 can be removed from the outer container 14.

In use, a nipple can be screwed onto the threaded neck of the connector 17. A volume of breast milk poured into the lid 20 may then be warmed by placing the lid 20 in hot water, and the child can then drink the warmed milk from the nipple coupled the connector 17, which may be connected to the lid 20.

According to one embodiment, the vessel 10 may be an insulated food container with a threaded neck lid 20 over two chambers 12, 14. When the disclosed vessel 10 is provided with a removable lid 20 it allows users to insert a coolant into the second chamber 96 while keeping the coolant separate from the inner chamber 46. When the threaded neck lid 20 is fixed to the large container 14, the user can attach the breast pump components to pump milk directly into the inner chamber 46. Alternatively, the user can attach a pour top to seal the vessel 10 for transport. The lid 20 can also be removed from the large container and placed on the lid 20 with a nipple to provide a warmable feeding bottle.

The features of this disclosed container allow users to pump milk directly into the inner container 12 and cool the milk for safe travel, storage and feeding.

Figure 3:
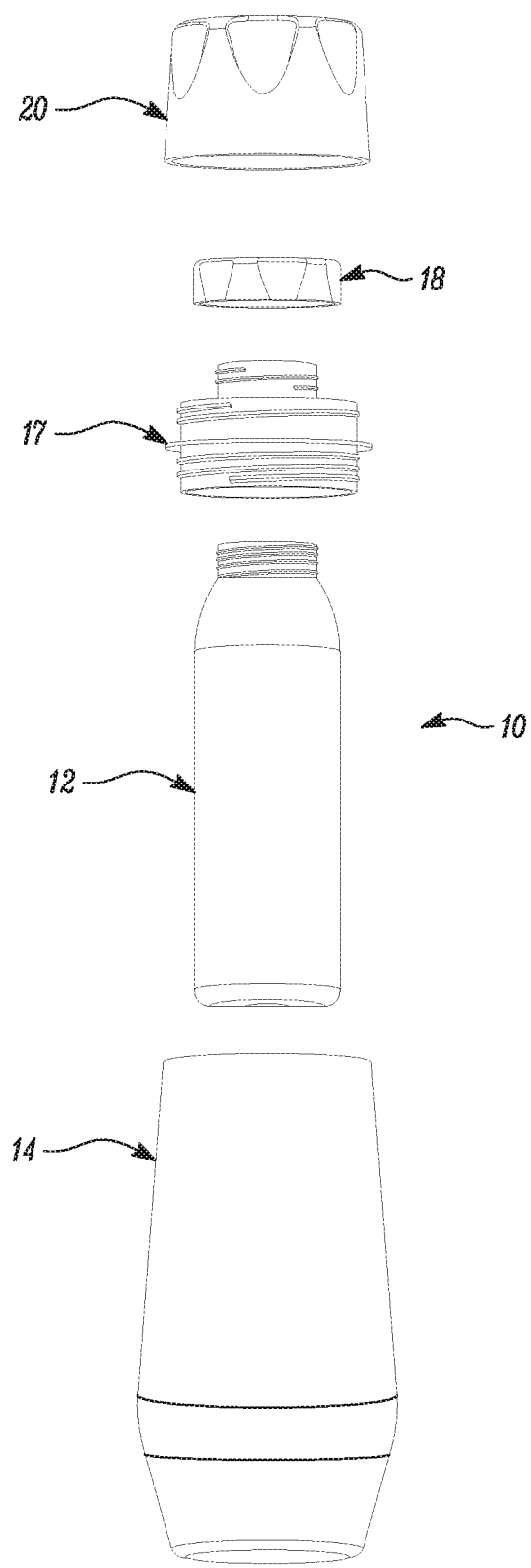
FIG. 3 is an exploded isometric view of the container illustrated in FIG. 1.

Referring to FIGS. 1 to 3, the vessel 10 includes an inner container 12, which is constructed to store a volume of liquid, for example breast milk. The vessel 10 further includes an outer container 14 and a connector 17. The outer container 14 is sized so as to at least partially enclose the inner container 12, to isolate the inner container 12 from a surrounding environment of the vessel 10, and assist in temperature regulation of the inner container 12 as will be explained in further detail below. The connector 17 secures the inner container 12 relative to the outer container 14.

The vessel 10 may further include a cap 18 that is securable to the inner container 12, the connector 17, or both the inner container 12 and the connector 17 to enclose the liquid stored within the inner container 12. As shown in the illustrated embodiment, the vessel 10 may include a lid 20 that is securable to the connector 17 such that the cap is enclosed within the lid 20.

Referring to FIGS. 4 to 7, the connector 17 has a body 19. The connector 17 includes a plurality of connector couplers that engage with complementary couplers on other components of the vessel 10 to couple the connector 17 to the respective other components. According to one embodiment, the plurality of connector couplers includes a first connector coupler 22, a second connector coupler 24, a third connector coupler 26, a fourth connector coupler 28, or any combination thereof.

As shown in the illustrated embodiment, the first connector coupler 22 and the second connector coupler 24 are similar, such that a complementary coupler that is coupleable to one of the first connector coupler 22 and the second connector coupler 24 will also be coupleable to the other of the first connector coupler 22 and the second connector coupler 24. According to one embodiment, the first connector coupler 22 and the second connector coupler 24 may include respective threads 23, 25, and the threads 23, 25 may have the same thread pitch. As shown, the threads 23, 25 may be similar such that they have the same major diameter, minor diameter, or both major diameter and minor diameter. The threads 23, 25 may include external threads, as shown. However, it will be appreciated by those of skill in the art that the threads 23, 25 may alternatively include internal threads.

According to one implementation, the first connector coupler 22 and the second connector coupler 24 are discontinuous such that a complementary coupler cannot transition from engagement with the first connector coupler 22 to engagement with the second connector coupler 24 without first disengaging from the connector 17. As shown the connector 17 may include an unthreaded section 27 between the first connector coupler 22 and the second connector coupler 24. The unthreaded section 27 may include a radial projection 30, which assists in forming a seal between the connector 17 and another component of the vessel 10 with the complementary coupler.

According to another implementation, the first connector coupler 22 and the second connector coupler 24 may be continuous such that a complementary coupler can transition from engagement with the first connector coupler 22 to engagement with the second connector coupler 24 without first disengaging from the connector 17. For example the threads 23, 25 may be a continuous unbroken thread with constant thread pitch.

According to one embodiment, the third connector coupler 26 may be different than the first connector coupler 22 and the second connector coupler 24, such that a complementary coupler that is coupleable to one of the first connector coupler 22 and the second connector coupler 24 will not be coupleable to the third connector coupler 26. According to one embodiment, the third connector coupler 26 may include threads 29. The threads 29 may have the same thread pitch as the threads 23, 25, or alternatively, the threads 29 may have a different thread pitch than the threads 23, 25. As shown, the threads 29 may have a smaller cross-sectional dimension, for example major diameter, minor diameter, or both major diameter and minor diameter, than the threads 23, 25. The threads 29 may include internal threads, as shown. However, it will be appreciated by those of skill in the art that the threads 29 may alternatively include external threads. The threads 29 may be the opposite type (internal/external) as the threads 23, 25. Alternatively the threads 29 may be the same type (internal/external) as the threads 23, 25.

According to one embodiment, the fourth connector coupler 28 may be complementary to the third connector coupler 26. According to one embodiment, the fourth connector coupler 28 may include threads 31. The threads 31 may have the same thread pitch as the threads 29. Additionally, the threads 31 may have a major diameter, minor diameter, or both major diameter and minor diameter, that facilitate threaded engagement with the threads 29. To be complementary to the threads 29, the threads 31 may be of the opposite type (internal/external) as the threads 29.

According to one implementation, the body 19 of the connector 17 is a monolithic, or one-piece, continuous, body. As shown, the connector 17 may define cross-sectional shape that is radially symmetrical about a central axis 32. As shown, the first connector coupler 22 may be radially centered about the central axis 32, the second connector coupler 24 may be radially centered about the central axis 32, and the third connector coupler 26 may be radially centered about the central axis 32.

The first connector coupler 22 and the third connector coupler 26 may be arranged such that a plane that is normal to the central axis 32 intersects both the first connector coupler 22 and the third connector coupler 26. As shown, the third connector coupler 26 may be radially spaced from the central axis 32 by a first distance, the first connector coupler 22 may be radially spaced from the central axis 32 by a second distance, and the second distance may be greater than the first distance. The connector 17, as well as any other of the components of the vessel 10 described herein, may be manufactured through injection molding, or an additive manufacturing process, for example.

Figures 8, 9:
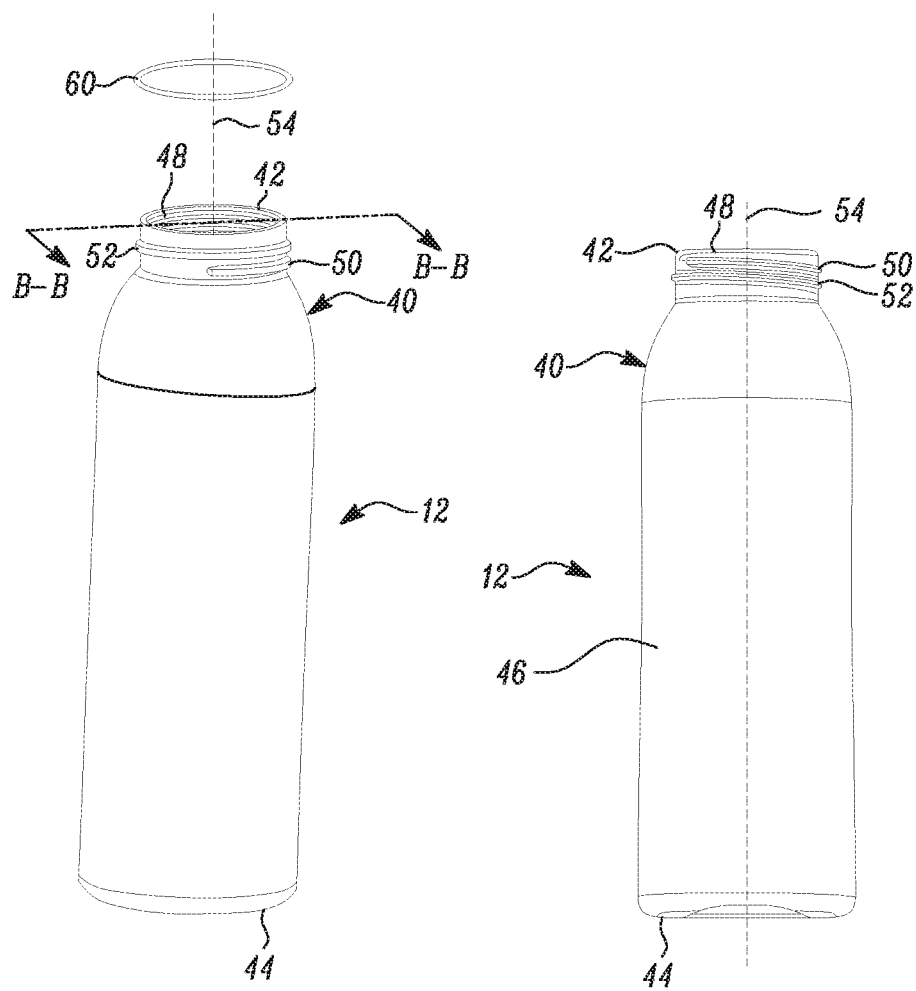
FIG. 8 is an isometric view of an inner chamber of the container illustrated in FIG. 1, according to one embodiment.
FIG. 9 is a cross-sectional view of the inner chamber illustrated in FIG. 7, along line B-B.

Referring to FIGS. 8 and 9, the inner container 12 has a body 40 that extends from a first end 42 of the inner container 12 to a second end 44 of the inner container 12 such that the body 40 partially encloses an inner chamber 46. The inner container 12 has an opening 48 proximate the first end 42, the opening 48 providing an access into the inner chamber 46. The inner container 12 may include an inner container coupler 50, for example proximate the first end 42. According to one embodiment, the inner chamber 46 has a volume of at least 8 ounces (oz.), for example at least 12 oz.

According to one embodiment, the inner container coupler 50 may be complementary to the third connector coupler 26. According to one embodiment, the inner container coupler 50 may include threads 52. The threads 52 may have the same thread pitch as the threads 29. Additionally, the threads 52 may have a major diameter, minor diameter, or both major diameter and minor diameter, that facilitate threaded engagement with the threads 29. To be complementary to the threads 29, the threads 52 may be of the opposite type (internal/external) as the threads 29.

According to one implementation, the body 40 of the inner container 12 is a monolithic, or one-piece, continuous, body. As shown, the inner container 12 may define cross-sectional shape that is radially symmetrical about a central axis 54. As shown, the inner container coupler 50 may be radially centered about the central axis 54.

The inner container 12 may include sealer 60, for example an O-ring, positioned between the inner container coupler 50 and the third connector coupler 26 such that engagement of the inner container coupler 50 with the third connector coupler 26 captures the sealer 60 between the inner container coupler 50 and the third connector coupler 26, thereby forming a liquid-proof barrier between the inner container coupler 50 and the third connector coupler 26.

According to one embodiment, the vessel 10 may include a number of sealers 60. Each of locations within the vessel 10 where couplers engage may, optionally, include a sealer 60 to provide or improve the quality of the barrier formed between the engaged couplers.

Figure 10:
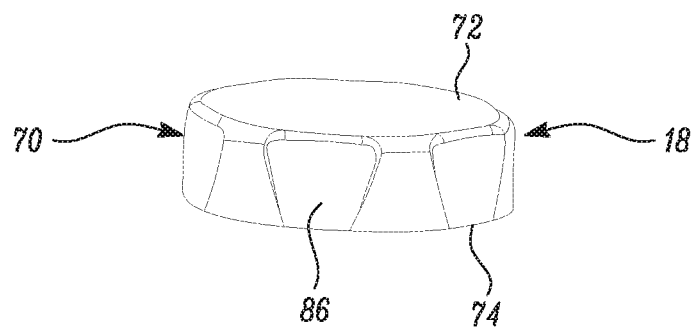
FIG. 10 is an isometric view of a cap of the container illustrated in FIG. 1, according to one embodiment.
Figure 11:
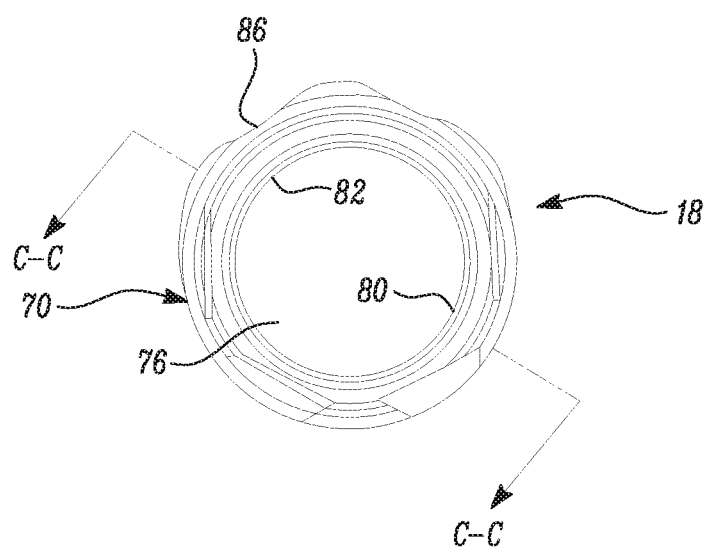
FIG. 11 is a bottom plan view of the cap illustrated in FIG. 10.
Figure 12:
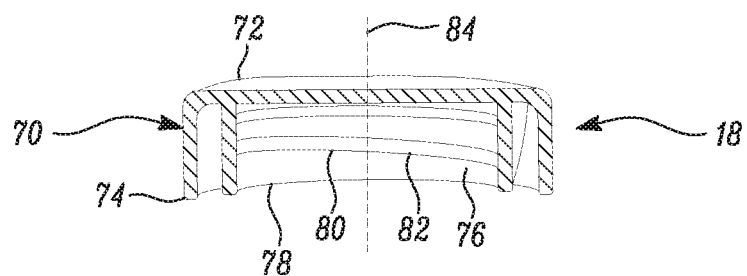
FIG. 12 is a cross-sectional view of the cap illustrated in FIG. 10, along line C-C.

Referring to FIGS. 10 to 12, the cap 18 has a body 70 that extends from a first end 72 of the cap 18 to a second end 74 of the cap 18 such that the body 72 partially encloses a cavity 76. The cap 18 has an opening 78 proximate the second end 74, the opening 78 providing an access into the cavity 76. The cap 18 may include a cap coupler 80, for example located within the cavity 76.

The first end 72 of the cap 18 may be closed, as shown in the illustrated embodiment. Alternatively, the first end 72 of the cap 18 may include a resealable aperture, for example a pour top or a sip top. The resealable aperture when open allows a user to consume the contents of the inner chamber 46 without removing the cap 18, and when closed maintains the liquid proof barrier enclosing the inner chamber 46.

According to one embodiment, the cap coupler 80 may be complementary to the fourth connector coupler 28, the inner container coupler 50, or both. According to one embodiment, the cap coupler 80 may include threads 82. The threads 82 may have the same thread pitch as the threads 31 and/or the threads 52. Additionally, the threads 82 may have a major diameter, minor diameter, or both major diameter and minor diameter, that facilitate threaded engagement with the threads 31 and/or the threads 52. To be complementary to the threads 31 and/or the threads 52, the threads 82 may be of the opposite type (internal/external) as the threads 31 and/or the threads 52.

According to one implementation, the body 70 of the cap 18 is a monolithic, or one-piece, continuous, body. As shown, the cap 18 may define cross-sectional shape that is radially symmetrical about a central axis 84. As shown, the cap coupler 80 may be radially centered about the central axis 84. The cross-sectional shape of the cap 18 may include one or more flats 86 to facilitate a user's application of a torque to the cap 18 to rotate the cap 18 about the central axis 84.

Figures 13, 14:
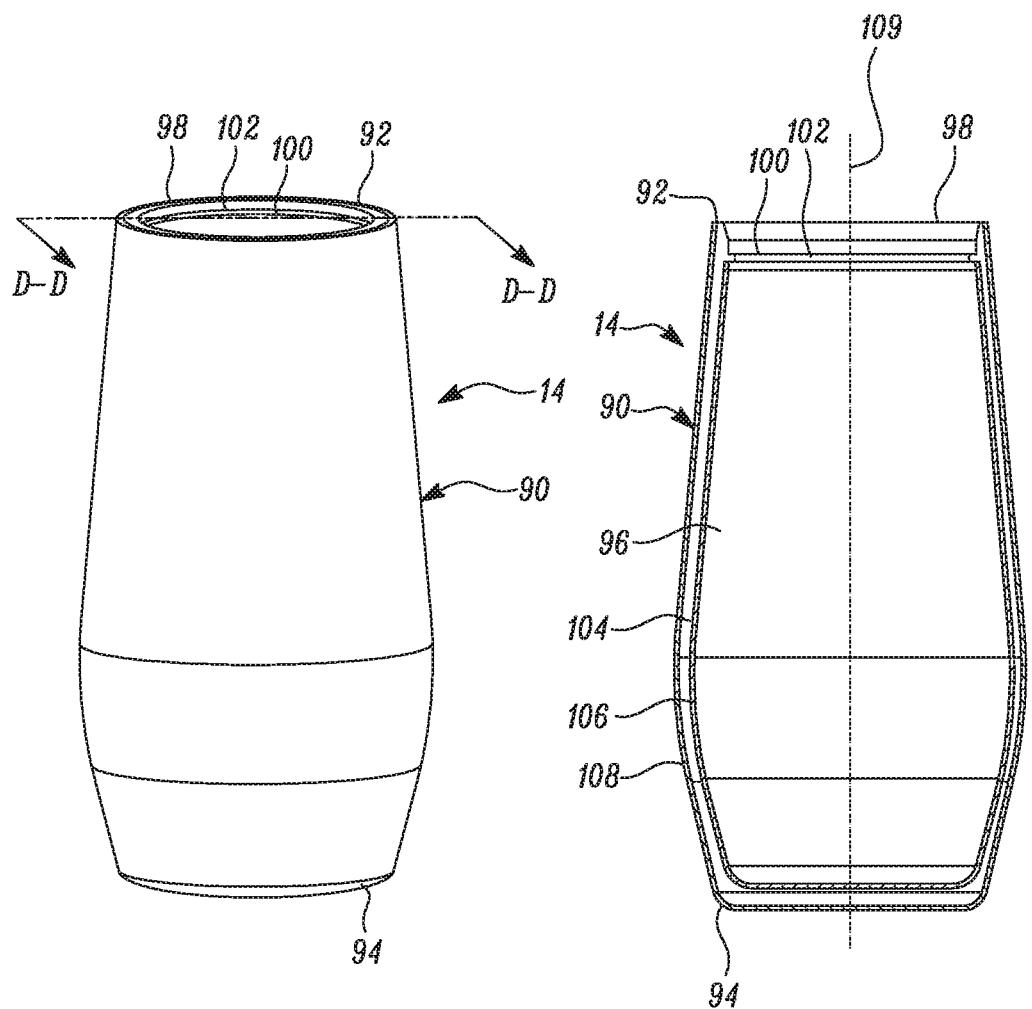
FIG. 13 is an isometric view of an outer chamber of the container illustrated in FIG. 1, according to one embodiment.
FIG. 14 is cross-sectional view of the outer chamber illustrated in FIG. 13, along line D-D.

Referring to FIGS. 13 and 14, the outer container 14 has a body 90 that extends from a first end 92 of the outer container 14 to a second end 94 of the outer container 14 such that the body 90 partially encloses an outer chamber 96. The outer container 14 has an opening 98 proximate the first end 92, the opening 98 providing an access into the outer chamber 96. The outer container 14 may include an outer container coupler 100, for example proximate the first end 92.

According to one embodiment, the outer container coupler 100 may be complementary to the first connector coupler 22 and the second connector coupler 24. According to one embodiment, the outer container coupler 100 may include threads 102. The threads 102 may have the same thread pitch as the threads 23, 25. Additionally, the threads 102 may have a major diameter, minor diameter, or both major diameter and minor diameter, that facilitate threaded engagement with the threads 23, 25. To be complementary to the threads 23, 25, the threads 102 may be of the opposite type (internal/external) as the threads 23, 25.

According to one implementation, the body 90 of the outer container 14 is a double walled body with a gap 104 between a first wall 106 and a second wall 108 that make up the double walled body. According to one embodiment, the gap 104 may include a vacuum, thereby improving thermal isolation of the outer chamber 96 from the surrounding environment of the vessel 10. As shown, the outer container 14 may define cross-sectional shape that is radially symmetrical about a central axis 109. As shown, the outer container coupler 100 may be radially centered about the central axis 109. The second wall 108 may define a cylindrical shape, or the second wall 108 may be tapered as shown.

Figure 15:
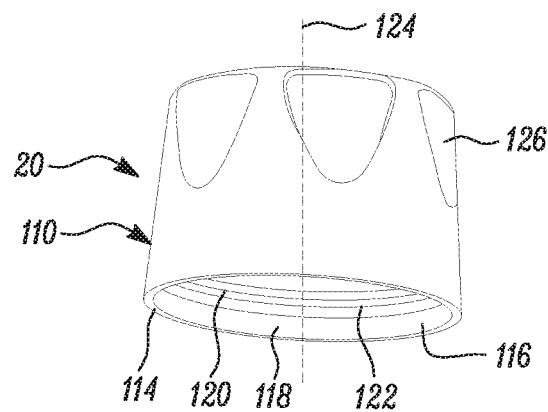
FIG. 15 is an isometric view of a lid of the container illustrated in FIG. 1, according to one embodiment.
Figure 16:
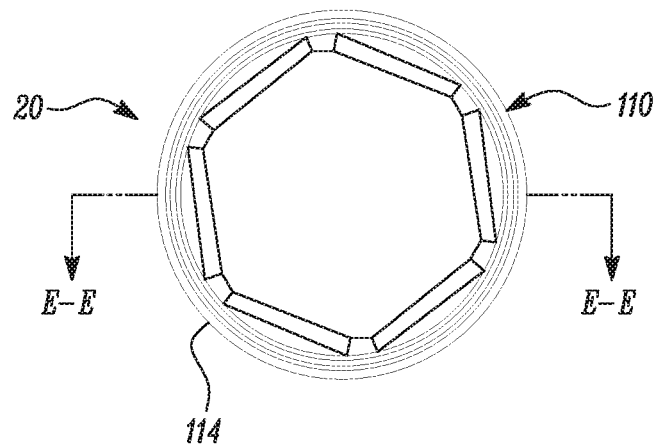
FIG. 16 is a bottom view of the lid illustrated in FIG. 15.
Figure 17:
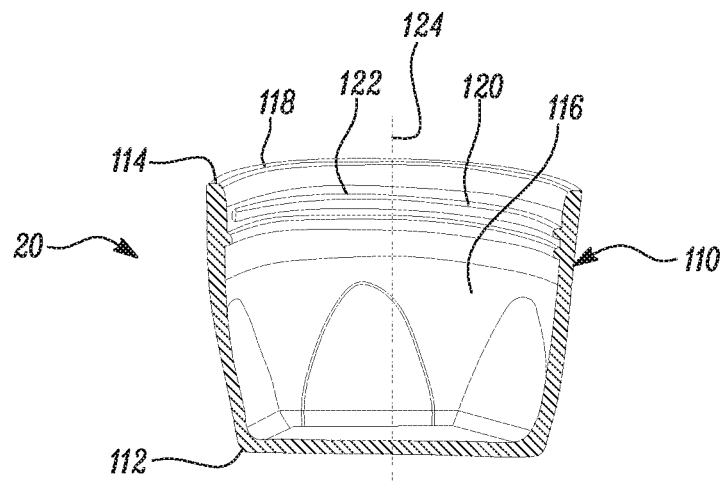
FIG. 17 is a cross-sectional view of the lid illustrated in FIG. 15, along line E-E.

Referring to FIGS. 15 to 17, the lid 20 has a body 110 that extends from a first end 112 of the lid 20 to a second end 114 of the lid 20 such that the body 110 partially encloses a cavity 116. The lid 20 has an opening 118 proximate the second end 114, the opening 118 providing an access into the cavity 116. The lid 20 may include a lid coupler 120, for example located within the cavity 116.

According to one embodiment, the lid coupler 120 may be complementary to the first connector coupler 22 and the second connector coupler 24. According to one embodiment, the lid coupler 120 may include threads 122. The threads 122 may have the same thread pitch as the threads 23, 25. Additionally, the threads 122 may have a major diameter, minor diameter, or both major diameter and minor diameter, that facilitate threaded engagement with the threads 23, 25. To be complementary to the threads 23, 25 the threads 122 may be of the opposite type (internal/external) as the threads 23, 25.

According to one implementation, the body 110 of the lid 20 is a monolithic, or one-piece, continuous, body. As shown, the lid 20 may define cross-sectional shape that is radially symmetrical about a central axis 124. As shown, the lid coupler 120 may be radially centered about the central axis 124. The cross-sectional shape of the lid 120 may include one or more flats 126 to facilitate a user's application of a torque to the lid 20 to rotate the lid 20 about the central axis 124.

Figure 18:
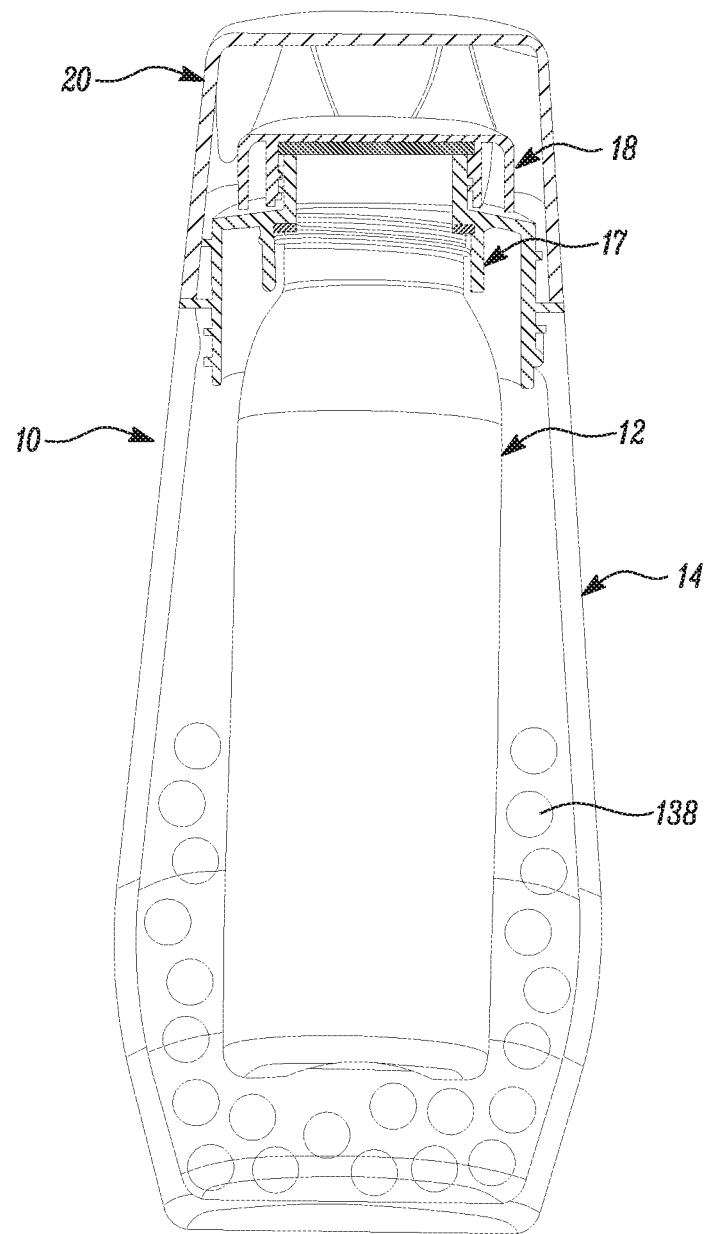
FIG. 18 is a cross-sectional view of the container illustrated in FIG. 1, along line F-F, in a fully assembled configuration.

Referring to FIGS. 1 to 18, the vessel 10 may have an assembled configuration (as shown in FIG. 18) in which the inner container 12, via the inner container coupler 50, is coupled to the connector 17, via the third connector coupler 26. For example, the inner container 12 may be coupled to the connector 17 by threadedly engaging the threads 52 with the threads 29. In the assembled configuration, the cap 18, via the cap coupler 80, is coupled to the connector 17, via the fourth connector coupler 28. For example, the cap 18 may be coupled to the connector 17 by threadedly engaging the threads 82 with the threads 31. When the connector 17 is coupled to both the inner container 12 and the cap 18 as described above, the inner chamber 46 is entirely enclosed within a liquid proof barrier.

In the assembled configuration, the outer container 14, via the outer container coupler 100, is coupled to the connector 17, via the first connector coupler 22. For example, the outer container 14 may be coupled to the connector 17 by threadedly engaging the threads 102 with the threads 23. When the connector 17 is coupled to both the inner container 12 and the outer container 14 as described above, the outer chamber 96 is entirely enclosed within a liquid proof barrier.

In the assembled configuration, the lid 20, via the lid coupler 120, is coupled to the connector 17, via the second connector coupler 24. For example, the lid 20 may be coupled to the connector 17 by threadedly engaging the threads 122 with the threads 25. As shown, in the assembled configuration one or more, for example all, of the central axis 32, the central axis 54, the central axis 84, the central axis 109, and the central axis 124 may be parallel, for example collinear.

Figures 19, 20:
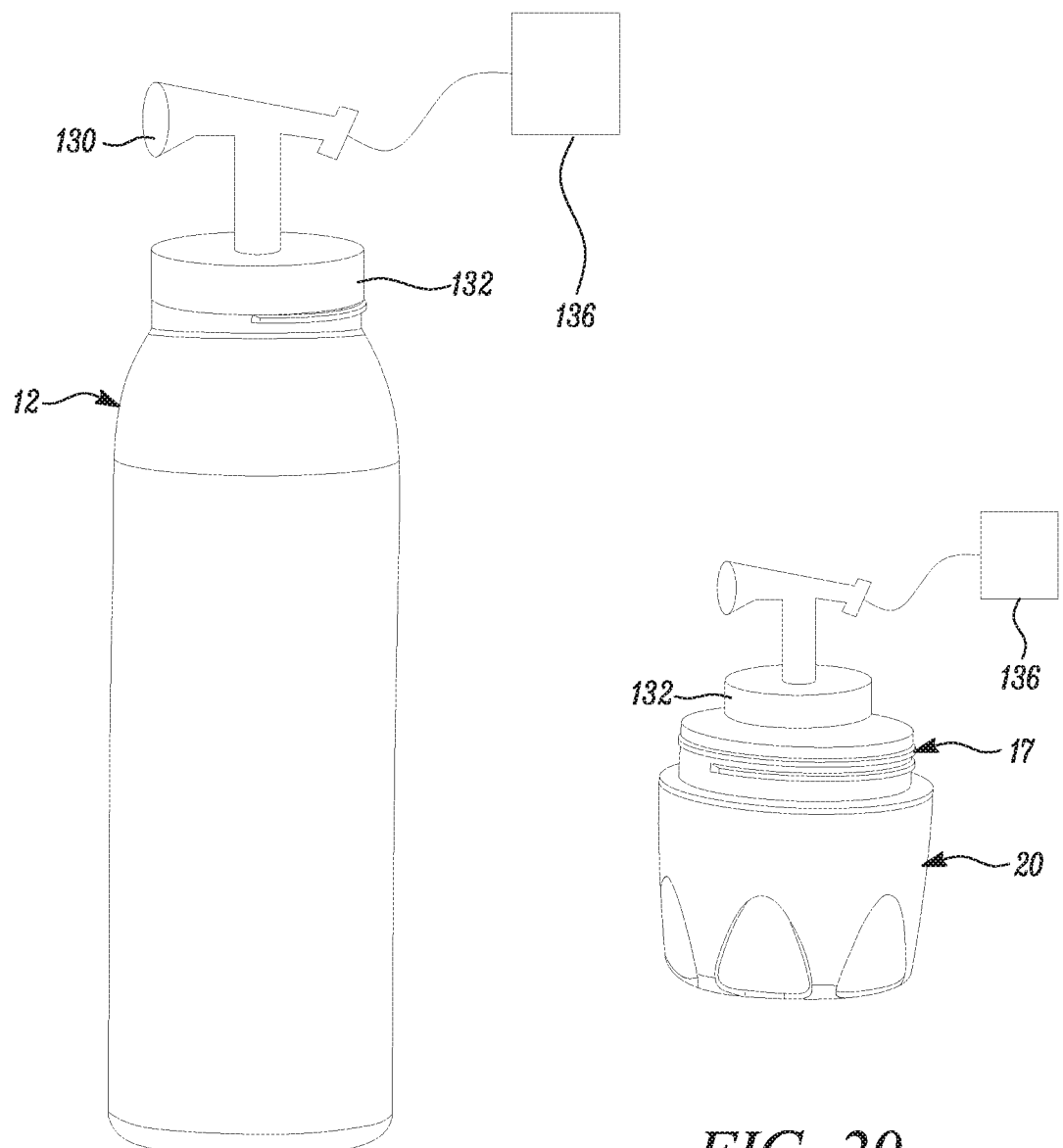
FIG. 19 is a front elevation view of a portion of the container illustrated in FIG. 1 in a pumping configuration.
FIG. 20 is a front elevation view of another portion of the container illustrated in FIG. 1 in a pumping configuration.

Referring to FIGS. 1 to 20, the vessel 10 may have a pumping configuration (as shown in FIGS. 19 and 20). As shown in FIG. 19, in the pumping configuration, a first portion of the vessel 10, for example the inner container 12, via the inner container coupler 50, is coupled to a breast shield 130, via a breast shield connector 132. According to one embodiment, the inner container 12 may be coupled to the breast shield 130 by threadedly engaging the threads 52 with complementary threads (not shown) of the breast shield connector 132.

In use, suction is applied by, for example, a pump 136 through the breast shield 130 while the breast shield 130 is in contact with a breast. The suction withdraws milk from the breast, and the withdrawn milk is transferred through the breast shield 130, though the breast shield connector 132, and into the inner chamber 46. After pumping is complete, the inner container 12 is decoupled from the breast shield 130. A cooling medium 138, for example ice, may be positioned within the outer chamber 96. The inner container 12, the outer container 14, the connector 17, and the cap 18 may then be coupled as described in reference to the assembled configuration, and as shown in FIG. 18, such that the withdrawn milk is isolated within the inner chamber 46 enclosed in a liquid proof barrier, with the cooling medium 138 in contact with the inner container 12 so as to lower the temperature of the withdrawn milk.

According to another embodiment, the vessel 10 may be used as an infuser. The inner container 12 may be a mesh material (or other material that allows liquid to pass through the body 40 of the inner chamber 12. The inner chamber 46 may be filled with an infusion material, such as tea leaves or coffee grounds. Liquid, for example hot water, may be poured into the outer chamber 96 and the hot water passes through the body 40 of the inner chamber 12 to interact with the infusion material, while the infusion material is maintained within the confines of the inner chamber 46. The infused liquid within the outer chamber 96 may then be consumed or poured into a separate container, for example the lid 20, for consumption.

As shown in FIG. 20, in the pumping configuration, a second portion of the vessel 10, for example the lid 20 and the connector 17, coupled by threaded engagement of the threads 122 and the threads 23, is coupled to the breast shield 130, via the breast shield connector 132. According to one embodiment, the second portion of the vessel 10 may be coupled to the breast shield 130 by threadedly engaging the threads 31 with complementary threads (not shown) of the breast shield connector 132.

In use, suction is applied by, for example, a pump 136 through the breast shield 130 while the breast shield 130 is in contact with a breast. The suction withdraws milk from the breast, and the withdrawn milk is transferred through the breast shield 130, though the breast shield connector 132, and into the cavity 116. After pumping is complete, the second portion of the vessel 10 is decoupled from the breast shield 130. The withdrawn milk may then be transferred to the inner chamber 46. The inner container 12, the outer container 14, the connector 17, and the cap 18 may then be coupled as described in reference to the assembled configuration, and as shown in FIG. 18, such that the withdrawn milk is isolated within the inner chamber 46 enclosed in a liquid proof barrier, with the cooling medium 138 in contact with the inner container 12 so as to lower the temperature of the withdrawn milk.

According to one embodiment, both the first portion of the vessel 10 and the second portion of the vessel 10 may be coupled to respective ones of the breast shield 130 such that milk may be withdrawn from two breasts simultaneously. The cooling medium 138 may be refilled/replaced, for example if the ice has melted, by decoupling the outer container 14 from the connector 17, removing the "old" cooling medium 138 from the outer chamber 96 and replacing/refilling at least a portion of the outer chamber 96 with "new" cooling medium 138.

Figures 21, 22:
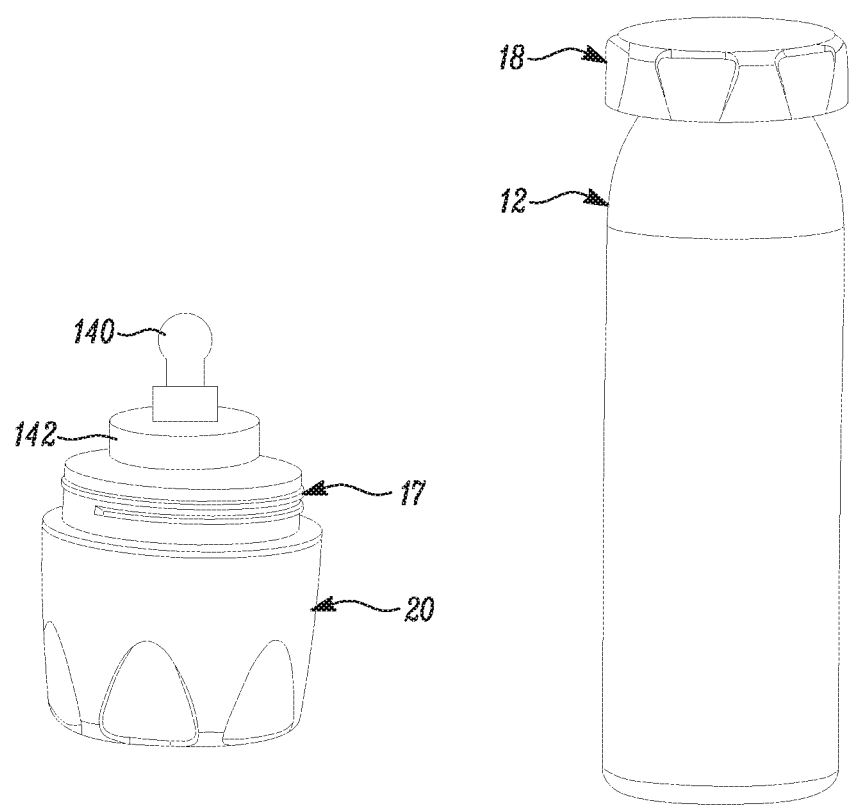
FIG. 21 is a front elevation view of a portion of the container illustrated in FIG. 1 in a feeding configuration.
FIG. 22 is a front elevation view of another portion of the container illustrated in FIG. 1 in a feeding configuration.

Referring to FIGS. 1 to 17 and 21 to 22, the vessel 10 may have a feeding configuration (as shown in FIGS. 21 and 22). As shown in FIG. 21, in the feeding configuration, the second portion of the vessel 10 is coupled to a feeding nipple 140, via a feeding nipple coupler 142. According to one embodiment, the second portion of the vessel 10 may be coupled to the feeding nipple 140 by threadedly engaging the threads 31 with complementary threads (not shown) of the feeding nipple coupler 142.

In use, prior to coupling of the second portion of the vessel 10 and the feeding nipple 140, a portion of the withdrawn milk within the inner chamber 46 is transferred to the cavity 116. As shown in FIG. 22, during feeding the cap 18 may be coupled to the inner container 12, for example by threadedly engaging the threads 52 with the threads 82, such that the withdrawn milk within the inner chamber 46 is isolated within the inner chamber 46 and enclosed in a liquid proof barrier. The inner container 12 may be placed within the outer chamber 96, for example such that the inner chamber 12 is resting on the cooling medium 138 rather than being supported by the connector 17. Alternatively, a second feeding nipple 140 may be coupled to the inner container 12 (in place of the cap 18 shown in FIG. 22) so that two children may be fed simultaneously.

The above description of illustrated embodiments, including what is described in the Abstract, is not intended to be exhaustive or to limit the embodiments to the precise forms disclosed. Although specific embodiments of and examples are described herein for illustrative purposes, various equivalent modifications can be made without departing from the spirit and scope of the disclosure, as will be recognized by those skilled in the relevant art.

Many of the methods described herein can be performed with variations. For example, many of the methods may include additional acts, omit some acts, and/or perform acts in a different order than as illustrated or described. The various embodiments described above can be combined to provide further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A vessel comprising:
   an outer container having a first coupler and an outer chamber;
   an inner container having a second coupler and an inner chamber to hold a liquid, the inner container receivable at least partially within the outer chamber such that a gap is formed between the inner container and the outer container;
   a connector having a third coupler that is complementary to the first coupler, and a fourth coupler that is complementary to the second coupler,
      wherein when both the first coupler is engaged with the third coupler and the second coupler is engaged with the fourth coupler, the outer chamber is entirely enclosed within a liquid-proof barrier, and
   a lid having a fifth coupler that is complementary to the third coupler.

2. The vessel of claim 1 wherein the connector has a sixth coupler that is complementary to the fifth coupler.

3. The vessel of claim 2, further comprising:
   a cap with a seventh coupler,
   wherein the connector has an eighth coupler that is complementary to the seventh coupler.

4. The vessel of claim 3 wherein the seventh coupler is complementary to the second coupler.

5. The vessel of claim 4 wherein engagement of any of the first, second, third, fourth, fifth, sixth, seventh, or eighth couplers with a complementary coupler restricts relative movement of the respective coupler and the complementary coupler in at least one degree of freedom due to interference between opposing surfaces of the respective coupler and the complementary coupler.

6. The vessel of claim 5 wherein:
the respective coupler and the complementary coupler both include threads,
rotation of the respective coupler relative to the complementary coupler about an axis engages the respective coupler and the complementary coupler, and
interference between the threads of the respective coupler and the corresponding coupler blocks translation of the respective coupler relative to the corresponding coupler along the axis.

7. The vessel of claim 6 wherein the respective coupler includes a sealer, the sealer positioned such that engagement of the respective coupler with the complementary coupler captures the sealer between the respective coupler and the complementary coupler such that a liquid-proof barrier is formed between the respective coupler and the complementary coupler.

8. The vessel of claim 3 wherein when each of: 1) the first coupler is engaged with the third coupler; 2) the second coupler is engaged with the fourth coupler; and 3) the seventh coupler is engaged with the eighth coupler, the inner chamber is entirely enclosed within a liquid proof barrier.

9. The vessel of claim 8 wherein when each of: 1) the first coupler is engaged with the third coupler; 2) the second coupler is engaged with the fourth coupler; and 3) the seventh coupler is engaged with the eighth coupler, no portion of the inner container directly contacts the outer container.

10. A connector comprising:
a first coupler that is complementary to a complementary coupler;
a second coupler that is complementary to the complementary coupler, and
a third coupler that is different than the first coupler and the second coupler such that the third coupler is not complementary to the complementary coupler;
wherein the first coupler is discontinuous with the second coupler such that the complementary coupler cannot transition from engagement with the first coupler to engagement with the second coupler without first disengaging from the connector, and
wherein the third coupler is radially inward of the first coupler and the second coupler.

11. The connector of claim 10 wherein the first coupler is radially centered about an axis, the second coupler is radially centered about the axis, and the third coupler is radially centered about the axis.

12. The connector of claim 11 wherein the first coupler and the second coupler are external threads with an identical thread pitch.

13. The connector of claim 11, further comprising a fourth coupler including features that are complementary to features of the third coupler.

14. The connector of claim 10 wherein the connector is a monolithic body.

* * * * *